US00PP12670P2

(12) United States Plant Patent
Klemm

(10) Patent No.: US PP12,670 P2
(45) Date of Patent: Jun. 4, 2002

(54) CARNATION PLANT NAMED 'KLECINCRE'

(75) Inventor: Siegfried Klemm, Stuttgart (DE)

(73) Assignee: Klemm & Sohn, Stuttgart (DE)

( * ) Notice: Subject to any disclaimer, the term of this patent is extended or adjusted under 35 U.S.C. 154(b) by 0 days.

(21) Appl. No.: 09/334,691

(22) Filed: Jun. 16, 1999

(51) Int. Cl.[7] ..... A01H 5/00
(52) U.S. Cl. ..... Plt./279
(58) Field of Search ..... Plt./279

(56) References Cited

PUBLICATIONS

UPOV–ROM GTITM Computer Database, 2000/05, GTI Jouve Retrieval Software, citation for 'Klecincre'.*

* cited by examiner

*Primary Examiner*—Bruce R. Campell
*Assistant Examiner*—Susan B. McCormick
(74) *Attorney, Agent, or Firm*—Howrey Simon Arnold & White, LLP

(57) ABSTRACT

The carnation plant 'Klecincre' is a natural mutation of 'Mizderella', but is distinguished by its cream-white flower color. The new and distinct variety shows the same attributes as its mother variety, including early flowering and blot upright stems, double flower with shallowly dentated petals, and the calyx doesn't split. The flowering is early and the stem production is high. 'Klecincre' has grayish green leaves with strong waxiness.

1 Drawing Sheet

BACKGROUND OF THE INVENTION

'Klecincre' is a new variety of carnation plant that originated as a sport of the variety 'Mizderella' (not patented), and was discovered in a greenhouse of our company in Stuttgart/Germany. The new plant is desirable for commercial greenhouse production because it has several of the desirable characteristics of its parent 'Mizderella', but is distinguished by its flower color. The mutation was selected in September 1994 because of its cream-white colored mature flower, a trait that distinguished it from its parent variety 'Mizderella', which has a cerise colored flower.

After selection, 'Klecincre' was vegetatively reproduced from stem cuttings in Stuttgart/Germany, Latina/Italy and Tquma D.N. Negev/Israel. By subjecting clones of this plant to successive generations of vegetative propagation, it was demonstrated that the distinctive characteristics of 'Klecincre' held true from generation to generation.

Traits of 'Klecincre' were recorded in Germany on Nov. 19, 1997. Observations were recorded from plants produced for cut flowers that were planted on May 5, 1997, pinched Jun. 3, 1997, and grown at a density of 19.2 plants per square meter. The results of trials indicated that 'Klecincre' had the same attributes as 'Mizderella', except for color.

The variety 'Klecincre' was propagated vegetatively, and, therefore, somatic mutations were a possibility. To-date, however, no variants that are different from the original variety have been noted. Additionally, since the sport 'Klecincre' was found in 1994, no instability of the new variety has been noted.

SUMMARY OF THE INVENTION

'Klecincre' is a carnation plant that has the same attributes as its parent 'Mizderella' but is distinguished by its cream-white petal color (both upper and lower surfaces), possessed by the mature flower. That cream-white petal color is best represented by 155A of The R.H.S. color code system.

BRIEF DESCRIPTION OF THE DRAWINGS

The carnation plant named 'Klecincre' is illustrated in the accompanying color photograph.

DETAILED BOTANICAL DESCRIPTION

The following is a detailed description of this new carnation as observed in Germany on Nov. 19, 1997 and Mar. 1, 2001. Color designations are compared to the 1986 edition of R.H.S. Colour Chart, first published in 1966 by The Royal Horticultural Society, London, England.

'Klecincre' has the same attributes as its parent 'Mizderella' but is distinguished by its cream-white petal color (both upper and lower surfaces), possessed by the mature flower. That cream-white petal color is best represented by 155A of The R.H.S. color code system.

Name: 'Klecincre'.
Parentage: Sport of 'Mizderella' (not patented).
Classification:
*Botanical.*—*Dianthus caryophyllus L.*
*Commercial.*—Carnation, standard type.
*Common name.*—Carnation.
Number of chromosomes: 2n=2x=30.

Plant

Height: Pinched plant about 110 cm tall.
Growing habit: Herbaceous, upright.
Blooming habit: Standard.
Blooming season: Perpetual.
Rooting time: About 12 days to initiate development of roots.

Stability of mature flower color: Stable.
Branching: About 7 stems arising from base of plant after pinching.
Disease resistance: Moderate to good. (Rated on scale from 1 (most susceptible) to 9 (most resistant)).
*Powdery mildew.*—7.
*Aphids.*—7.
Temperature tolerance: Moderate. (Rated on scale from 1 (most susceptible) to 9 (most resistant)).
*Heat.*—5.
*Cold.*—5.

Foliage

Color, dorsal: Blue-green RHS 133B.
Color, ventral: Blue-green RHS 133B.
Size:
*Length.*—12 cm.
*Width.*—11 mm.
*Thickness.*—0.5 mm.
Petiole: None.
Quantity: Varies with season and cultural conditions.
Shape: Linear, pointed; margin entire; slight leaf wrinkling; leaf tip acuminate.
Texture: Waxy, glabrous.
Ribs: Central, keeled.
Arrangement: Two leaves opposite, at node.

Stem

Stem color: Blue-green RHS 133C.
Length of internodes: About 7 cm.
Stem quality: Excellent. (Rated on scale from 1 (very weak and soft) to 9 (very strong and stiff)). Strength: 9.

Bud

Inflorescence height from ground: About 104 cm.
Shape: Ellipsoid; topview circular; sideview convex.
Color: Green RHS 141C.
Length: 3 cm.
Diameter: 2.2 cm.
Number of flowers per inflorescence: 1.
Peduncle: None.
Calyx: Campanulate.
*Number of sepals.*—6, fused.
*Length.*—3.5 cm.
*Width.*—2.8 cm.
*Color.*—Inside: light green RHS 149D. Outside: green RHS 143C.

Bloom

Shape: Top view circular; sideview convex.
Size: 8 cm.
Borne: 1 flower per stem; stem length about 85 cm.
Color: Mature flower: cream-white RHS 155A.
Keeping quality: Average lastingness; blooms last about 10 days as cut flowers; about 16 days on plant.
Fragrance: Absent.

Petals

Number: About 50.
Length: 46 mm.
Width: 31 mm.
Texture: Leathery.
Form: Fan shaped; margin is shallowly serrated.
Appearance: Velvety.

Reproductive organs

Stamens: About 5 per flower.
Anthers: About 5 per flower; 1.5 mm long, 0.5 mm wide; color is white, ranging from RHS 158D to RHS 185C.
Filaments: Length 1.8 cm.
Pistil: Length 3 cm when flower fully open; each flower has one ovary with 2–4 styles; each style has one stigma.
Stigma: Color is cream, ranging between RHS 159C and RHS 185C.
Style: Color is cream, ranging between RHS 159C and RHS 185C.
Ovary: Spindle shaped, ribbed surface; 1.1 cm long, 0.9 cm wide; color is light green RHS 145A.
Pollen: Light yellow RHS 2D.
Fertility: Male — fair; female — fair; approximately 50% of pollinated ovaries produce seed; variety is not self-pollinated.

What is claimed is:

1. A new and distinct variety of carnation plant named 'Klecincre', substantially as herein described and shown, characterized by its cream-white color.

* * * * *

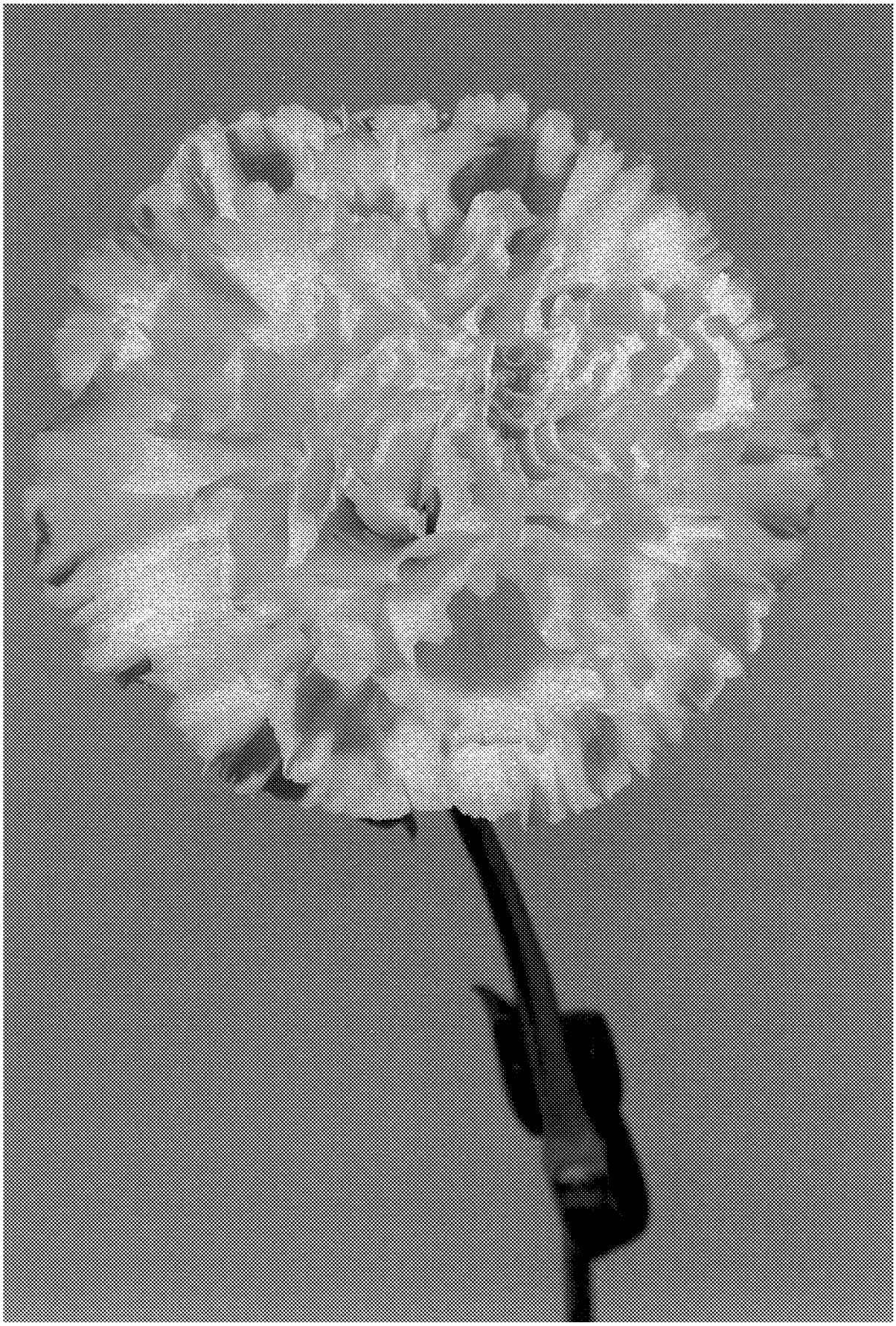

UNITED STATES PATENT AND TRADEMARK OFFICE

CERTIFICATE OF CORRECTION

PATENT NO. : PP 12,670 P2
DATED : June 4, 2002
INVENTOR(S) : Siegfried Klemm

It is certified that error appears in the above-identified patent and that said Letters Patent is hereby corrected as shown below:

Title page,
Item [57], ABSTRACT,
Delete "The carnation plant 'Klecincre' is a natural mutation of 'Mizderella', but is distinguished by its cream-white flower color. The new and distinct variety shows the same attributes as its mother variety, including early flowering, and blot upright stems, double flower with shallowly dentated petals, and the calyx doesn't split. The flowering is early and the stem production is high. 'Klecincre' has grayish green leaves with strong waxiness.", and insert -- A new variety of carnation plant named 'Klecincre'. This variety is a sport of its parent 'Mizderella', but is distinct from the parent by way of its cream-white flower color. --

Column 4,
Line 43, delete "A new and distinct variety of carnation plant named 'Klecincre', substantially as herein described and shown, characterized by its cream-white color.", and insert -- A new and distinct carnation plant named 'Klecincre', substantially as described and illustrated herein. --

Signed and Sealed this

Twenty-sixth Day of November, 2002

*Attest:*

*Attesting Officer*

JAMES E. ROGAN
*Director of the United States Patent and Trademark Office*